US005544216A

United States Patent [19]

Norhager

[11] Patent Number: 5,544,216

[45] Date of Patent: Aug. 6, 1996

[54] X-RAY EXAMINATION APPARATUS

[75] Inventor: Yngve Norhager, Vallentuna, Sweden

[73] Assignee: Siemens Elema AB, Solna, Sweden

[21] Appl. No.: 450,706

[22] Filed: May 25, 1995

[30] Foreign Application Priority Data

Jun. 2, 1994 [SE] Sweden .................................. 9401904

[51] Int. Cl.$^6$ ........................................................ A61B 6/06

[52] U.S. Cl. .............................................. 378/149; 378/41

[58] Field of Search ................................ 378/41, 42, 124, 378/134, 145, 147, 149, 150, 151, 152, 37

[56] References Cited

U.S. PATENT DOCUMENTS

| | | | |
|---|---|---|---|
| 3,857,039 | 12/1974 | Franke et al. | 378/134 X |
| 4,641,335 | 2/1987 | Hahn | 378/41 X |
| 4,766,603 | 8/1988 | Okabe et al. | 378/41 X |
| 5,299,250 | 3/1994 | Styrnol et al. | 378/151 X |

*Primary Examiner*—David P. Porta
*Attorney, Agent, or Firm*—Hill, Steadman & Simpson

[57] ABSTRACT

An x-ray examination apparatus has an x-ray tube having an anode dish with a number of selectively activatable focal spots that are arranged such that all of the focal spots are intersected by a common straight line. In order to obtain an x-ray examination apparatus with a primary radiation diaphragm that can be shifted in a very simple way such that it is quickly brought into a position that is matched to the current focal spot generated on the anode dish, a mechanism is provided for shifting the primary radiation diaphragm along the straight line when switching from one focal spot to another.

5 Claims, 1 Drawing Sheet

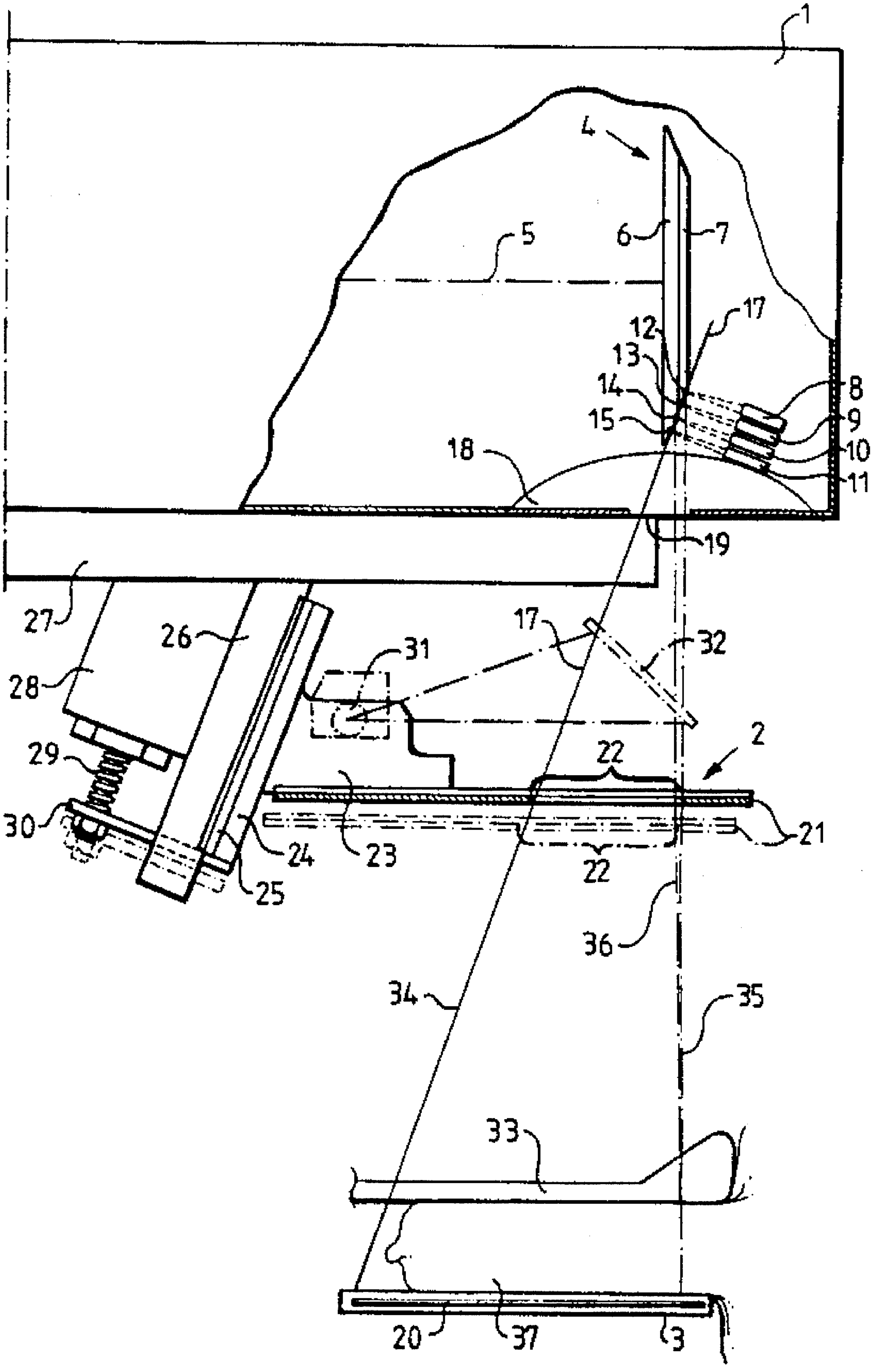
1
4
5
6
7
8
9
10
11
12
13
14
15
17
18
19
2
20
21
22
23
24
25
26
27
28
29
30
31
32
33
34
35
36
37
3

X-RAY EXAMINATION APPARATUS

BACKGROUND OF THE INVENTION

1. Field of the Invention

The present invention is directed to an X-ray examination apparatus of the type having an x-ray tube having an anode dish with optionally activatable focal spots that are arranged such that all are intersected by a common straight line, and having a displaceable primary radiation diaphragm.

2. Description of the Prior Art and Related Subject Matter

German OS 3 136 806, corresponding to U.S. Pat. No. 4,464,778, discloses an x-ray examination apparatus of this type. The anode dish in the x-ray tube, which is rotatable around its own axis, is provided with two different focal spot paths inclined relative to the dish plane. The x-ray tube also has two cathodes, each cathode being directed onto a respective focal spot path. A focal spot is respectively generated on each focal spot path by the cathodes, and the focal spot of the one path is, for example, larger than that of the other path. As a result, the operator can activate that cathode and thus that focal spot, which the operator considers most suitable in an examination, for example in a mammography examination. Since the focal spots are present on the anode dish with a specific spacing from one another, the primary radiation diaphragm must also be displaced when a switch is undertaken from the one to the other focal spot so that the x-ray cone remains directed onto the subject table, i.e., so that it exactly covers the sheet of x-ray film that is inserted into or under the subject table. In the aforementioned German published application, the primary radiation diaphragm or the primary radiation diaphragm housing, can only be laterally displaced up to two limit positions, whereby the primary radiation diaphragm is set with reference to one focal spot in the one limit position and is set with reference to the other focal spot in the other limit position. It has not been taken into consideration in this x-ray examination apparatus that these focal spots, in addition to being offset from one another in a lateral spacing at the anode dish, are also offset spaced from one another in height, i.e. with different spacings from the primary radiation diaphragm or from the subject table. Switching to a focal spot that lies closest to the primary radiation diaphragm thus can lead to an undesirable spread of the x-ray field outside the exposure region.

The Siemens brochure "Mammomat" describes a mammography apparatus having an x-ray tube that is disclosed in German OS 3 136 806. The apparatus is also provided with a primary radiation diaphragm housing that is pivotable into two limit positions with articulated arms, so that the primary radiation diaphragm is matched to the current focus point in each limit position. As a result of the primary radiation diaphragm housing describing an arcuate motion given a displacement from one to the other limit position, it is displaced laterally as well as in height. In this way, the primary radiation diaphragm is also matched in height for the focal spot that lies closest to the subject table.

Co-Pending U.S. patent application Ser. No. 08/245,249 ("X-ray Tube with Multiple Differently Sized Focal Spots, Knott)" filed Mar. 3, 1994, discloses an x-ray tube with an anode dish at which four focal spots can be generated by the same number of cathodes. The focal spot paths of the anode dish lie on a common plane that is inclined relative to the dish plane, so that all four focal spot that can be generated are intersected by a common, imaginary straight line that proceeds along the inclined plane. A primary radiation diaphragm that is employed in conjunction with the mammography apparatus described in the Siemens brochure "Mammomat" cannot be used in combination with the anode dish disclosed in this unpublished German patent application since this primary radiation diaphragm can only be brought into two limit positions that are respectively matched to one focal spot. Due to the arcuate motion that the primary radiation diaphragm describes given a displacement from one to the other limit position, there is no position between the two limit positions wherein the diaphragm can be matched to another focal spot capable of being produced at the anode dish, since all of the focal spots are intersected by a common straight line.

SUMMARY OF THE INVENTION

An object of the present invention is to provide an x-ray examination apparatus of the type initially described having a primary radiation diaphragm that can be shifted in a very simple way such that it can be quickly brought into a position that is matched to the current focal spot of an anode dish having a plurality of such activatable focal spots.

This object is inventively achieved in an x-ray examination apparatus having a primary radiation diaphragm that is displaced along the straight line which intersects the focal spot when being switched from one focal spot to another. As a result, the primary radiation diaphragm can always be brought into an optimum position for the current focal spot, regardless of the number of focal spots. It is thus assured that the position and size of the exposure field is always the same.

In a development of the invention, the primary radiation diaphragm is attached to a holder that is arranged parallel to the straight line. A displacement of the primary radiation diaphragm along the straight line can thus ensue in a very simple way.

The displacement of the primary radiation diaphragm can ensue by means of a motor, preferably a stepping motor. This permits the primary radiation diaphragm to be brought into an optimum position for the current focal spot in a simple and uncomplicated way when switching from one focal spot to another.

In another development of the invention the primary radiation diaphragm is displaced by a distance that corresponds to the spacing between the focal spots between which a switch is made multiplied by a factor that is selected such that the size of the exposure area is retained.

DESCRIPTION OF THE DRAWINGS

The single FIGURE is a side view, partly broken away and partly in section, of an exemplary embodiment of an x-ray examination apparatus constructed in accordance with the principles of the present invention.

DESCRIPTION OF THE PREFERRED EMBODIMENTS

Somewhat simplified, the drawing shows selected parts of an x-ray examination apparatus of the invention in the form of a mammography apparatus. The apparatus includes an x-ray tube 1, a primary radiation diaphragm 2 and a subject table 3, the distance between the x-ray tube 1 and the subject table 3 is not being drawn to scale. The x-ray tube 1 is of a type shown and described in unpublished German patent application 4 323 928, discussed above. The x-ray tube 1 thereby has an anode dish 4 that is rotatable around its own axis 5. The anode dish 4 is provided with two focal spot paths 6 and 7 that are generated on a common plane inclined relative to the dish plane. Four focus points 12 through 15 spaced from one another on the dish plane can be generated by means of cathodes 8 through 11 that are directed toward the inclined dish plane. As shown in the drawing, all focal spots that can be generated are intersected by a common straight line 17. The x-ray tube 1 is provided with an opening 18 and with a fixed coarse diaphragm 19 that serves the purpose of collimating the x-ray beam generated by one of the focal spots 12 through 15 and directing it onto the subject table 3, in which a sheet 20 of x-ray film is applied before an exposure.

The primary radiation diaphragm 2 serves the purposes of gating the x-rays from the x-ray tube 1, i.e., from one of the focal spots 12, 13, 14 or 15 and of finely setting the beam. The primary diaphragm 2 is composed here of a plate 21 made of material impermeable to x-rays and having an approximately quadratic opening 22. The plate 21 is secured to a carriage 24 via a bracket 23. The carriage 24 is in turn connected to a holder 26 via linear ball bearings 25 and is displaceable along the holder 26 with the ball bearings 25. The holder 26, which is rigidly connected to the tube 1 via a fastener 27, is attached angled such that it proceeds parallel to the straight line 17. A stepping motor 28 is also attached to the holder 26, this stepping motor 28 controlling a screw 29 such that it is rotated in a threaded bore so as to displace another bracket 30 in the longitudinal direction of the screw 29. The free end of the screw 29 is connected to the carriage 24 via the elongated bracket 30. The primary radiation diaphragm 2 is also provided with a lamp 31 and a mirror 32 that are preferably secured to the bracket 23 or to the plate 21. The purpose of the lamp 31 and of the mirror shall be set forth later.

Before an x-ray examination, the subject, such as a breast 37 of a patient, is placed at the subject table 3. Subsequently, the breast 37 is compressed in a known way by a compression plate 33. As shown in this exemplary embodiment, the cathode 8 of the x-ray tube 1 generates a focal spot 12 that in turn directs an x-ray beam that is suitable for this examination onto the subject table 3. The x-ray are limited by the diaphragm aperture 22 so that they are incident at the subject table 3 within a predetermined area. The ray field limited with the diaphragm aperture 22 is marked with straight lines referenced 34 and 35 in the drawing. When, by influencing the cathode 10, the physician then decides instead to generate the focal spot 14, the carriage 24, and thus the diaphragm plate 2, is displaced along the holder 26 by the motor 28, the screw 29 and the bracket 30. The amount of displacement is a distance that corresponds to the spacing between the previously activated focal spot 12 and the focal spot 14 multiplied by a factor that is selected such that the size of the exposure area on the subject table 3 is retained. The new position of the diaphragm plate 21, or of the carriage 24, is shown with dot-dash lines. Since the holder 26 is arranged parallel to the straight line 17, the diaphragm aperture 22 is now shifted along the line 17, i.e., downwardly and laterally, whereby the displacement of the diaphragm plate 21 is somewhat shorter than the spacing between the focal spots 12 and 14. As already set forth, the exposure area on the subject table 3 is retained in this way. The limits of the ray field after the switchover to the focal spot 14 are referenced 34 and 36.

Given a switch from the focal spot 14 to another desired focal spot 12, 13 or 15 capable of being generated, the diaphragm aperture 22—as set forth—is shifted along the straight line 17, so that the diaphragm aperture 22 is always brought into a position that is optimal for the activated focal spot. The stepping motor 28, which displaces the carriage 24 for the diaphragm plate 21 such that the diaphragm plate 21 assumes these optimum positions when the desired focal spots are activated, is controlled with a microprocessor (not shown or described in greater detail here since it is known) on the basis of a control program provided for this purpose.

As a result of the described displacement of the primary radiation diaphragm 2, the diaphragm 2 can always be brought quickly and simply into an optimum position for the activated focal spot, regardless of the number of focal spots that can be generated on an anode dish of the type described in the exemplary embodiment.

The holder 26 for the diaphragm plate 21 can be replaced by a rail system (not shown) having crossed rails attached perpendicularly relative to one another that can be displaced relative to one another. Given such a structure of the holder as well this being preferably attached perpendicularly relative to the diaphragm plate 21, the diaphragm plate 21 can be made to shift along the straight line 17.

The lamp 31 and the mirror 31 mentioned above which are preferably secured to the primary radiation diaphragm 2, serve the purpose of illuminating the exposure field at the subject table 3 before an exposure, this exposure field to be subsequently irradiated with x-rays. As a result of the illuminated field, it is simpler for the operator to place the x-ray subject 37 into an optimum position on the subject table 3. The illuminated field is also an indication of the size and position of the exposure field. The mirror 32 is subsequently pushed aside in a known way so that the beam path between the focal spot and the subject is kept free.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray examination apparatus comprising:

an x-ray tube having an anode dish with a plurality of selectively activatable focal spots, all of said focal spots being disposed on said anode dish intersected by a common straight line, an x-ray beam being emitted from a selected one of said focal spots which is activated;

a primary radiation diaphragm disposed so that said x-ray beam passes therethrough; and means for displacing said primary radiation diaphragm along said straight line when switching from one of said focal spots to another of said focal spots for matching a position of said primary radiation diaphragm to the position of the selected focal spot which has been activated.

2. An x-ray examination apparatus as claimed in claim 1 wherein said means for displacing comprises a mount, to which said primary radiation diaphragm is attached, disposed parallel to said straight line.

3. An x-ray examination apparatus as claimed in claim 1 wherein said means for displacing comprises a motor.

4. An x-ray examination apparatus as claimed in claim 3 wherein said motor comprises a stepping motor.

5. An x-ray examination apparatus as claimed in claim 1 wherein said focal spots have a spacing respectively therebetween, and wherein said means for displacing comprises means for shifting said primary radiation diaphragm by a distance corresponding to the spacing from said one of said focal spots to said another of said focal spots multiplied by a factor for maintaining a selected size of an exposure area irradiated by said x-ray beam.

* * * * *